United States Patent
Noguchi et al.

(10) Patent No.: US 10,054,693 B2
(45) Date of Patent: *Aug. 21, 2018

(54) X-RAY IMAGING DEVICE WITH PROTECTIVE COVER

(71) Applicant: FUJIFILM CORPORATION, Minato-ku, Tokyo (JP)

(72) Inventors: Shinsuke Noguchi, Kanagawa (JP); Yusuke Kitagawa, Kanagawa (JP); Takeyasu Kobayashi, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 380 days.

This patent is subject to a terminal disclaimer.

(21) Appl. No.: 14/960,457

(22) Filed: Dec. 7, 2015

(65) Prior Publication Data

US 2016/0081640 A1 Mar. 24, 2016

Related U.S. Application Data

(63) Continuation of application No. 13/947,094, filed on Jul. 21, 2013, now Pat. No. 9,232,926.

(30) Foreign Application Priority Data

Aug. 1, 2012 (JP) ................................ 2012-171283

(51) Int. Cl.
*H01L 27/146* (2006.01)
*H01L 27/148* (2006.01)
(Continued)

(52) U.S. Cl.
CPC ............ *G01T 1/244* (2013.01); *A61B 6/4423* (2013.01); *G01T 1/247* (2013.01);
(Continued)

(58) Field of Classification Search
CPC ....... A61B 6/00; A61B 6/4233; A61B 6/4411; A61B 6/4423; A61B 6/52; G03B 42/04;
(Continued)

(56) References Cited

U.S. PATENT DOCUMENTS

| 7,189,972 B2 | 3/2007 | Ertel |
| 8,256,957 B1 | 9/2012 | Barnes |

(Continued)

FOREIGN PATENT DOCUMENTS

| EP | 2362240 A1 | 8/2011 |
| JP | H07-313561 A | 12/1995 |

(Continued)

OTHER PUBLICATIONS

English language translation of the following: Office action dated Dec. 20, 2016 from the JPO in a Japanese patent application No. 2012-171283 corresponding to the instant patent application. This office action translation is submitted now in order to supplement the understanding of the cited references which are being disclosed in the instant Information Disclosure Statement.

(Continued)

*Primary Examiner* — Anastasia Midkiff
(74) *Attorney, Agent, or Firm* — SOLARIS Intellectual Property Group, PLLC

(57) ABSTRACT

There is provided a radiographic imaging device including: a radiographic imaging device main body; and a protective cover that is removably applied to a surface of the radiographic imaging device main body, wherein a thickness of the radiographic imaging device main body, with the protective cover applied, is less than or equal to 16 mm.

7 Claims, 12 Drawing Sheets

(51) Int. Cl.
*H01L 27/144* (2006.01)
*G01T 1/24* (2006.01)
*A61B 6/00* (2006.01)
*G03B 42/04* (2006.01)

(52) U.S. Cl.
CPC .... *H01L 27/1462* (2013.01); *H01L 27/14618* (2013.01); *A61B 6/4411* (2013.01); *A61B 6/52* (2013.01); *G03B 42/04* (2013.01); *H01L 27/14601* (2013.01); *H01L 27/14806* (2013.01)

(58) Field of Classification Search
CPC ......... G03B 42/047; G01T 1/24; G01T 1/244; G01T 1/247; G01N 2223/301; H01L 27/144; H01L 27/146; H01L 27/14601; H01L 27/14618; H01L 27/1462; H01L 27/14658; H01L 27/148; H01L 27/14806
See application file for complete search history.

(56) References Cited

U.S. PATENT DOCUMENTS

| | | | |
|---|---|---|---|
| 9,232,926 B2 * | 1/2016 | Noguchi | .............. A61B 6/4411 |
| 2006/0227937 A1 | 10/2006 | Unger | |
| 2008/0311322 A1 | 12/2008 | Haskin | |
| 2009/0065703 A1 * | 3/2009 | Jadrich | ................ G01T 1/2928 |
| | | | 250/370.11 |
| 2012/0018830 A1 * | 1/2012 | Lin | ................... H01L 27/14618 |
| | | | 257/432 |
| 2012/0153172 A1 | 6/2012 | Sumi | |
| 2014/0037070 A1 | 2/2014 | Noguchi Shinsuke | |

FOREIGN PATENT DOCUMENTS

| | | |
|---|---|---|
| JP | 2003-207864 A | 7/2003 |
| JP | 2006-293368 A | 10/2006 |
| JP | 2008-233300 A | 10/2008 |
| JP | 2010-071726 A | 4/2010 |
| JP | 2010-276659 A | 12/2010 |
| JP | 2012-123005 A | 6/2012 |
| JP | 2012-125381 A | 7/2012 |
| JP | 2012-132703 A | 7/2012 |
| WO | 94/10605 A | 5/1994 |

OTHER PUBLICATIONS

Japanese Office Action dated Feb. 9, 2016, issued for the corresponding Japanese Patent Application No. 2012-171283.
Extended European Search Report dated Nov. 13, 2013 issued in corresponding EP Application No. 13177526.4.
Cannon CXDI Wireless Series brochure, Nov. 2011, Healthcare Solutions Division, p. 1.
Jou, Heat Transfer Investigations of a Nano-porous Silicon Film Deposited on a Flexible Cyclic Olefin Copolymers Substrate, Dec. 2007, Key Engineering Materials vols. 364-366, pp. 931 and 934.
Japanese Office Action dated Jun. 23, 2015 issued in corresponding Japanese Patent Application No. 2012-171283.

* cited by examiner

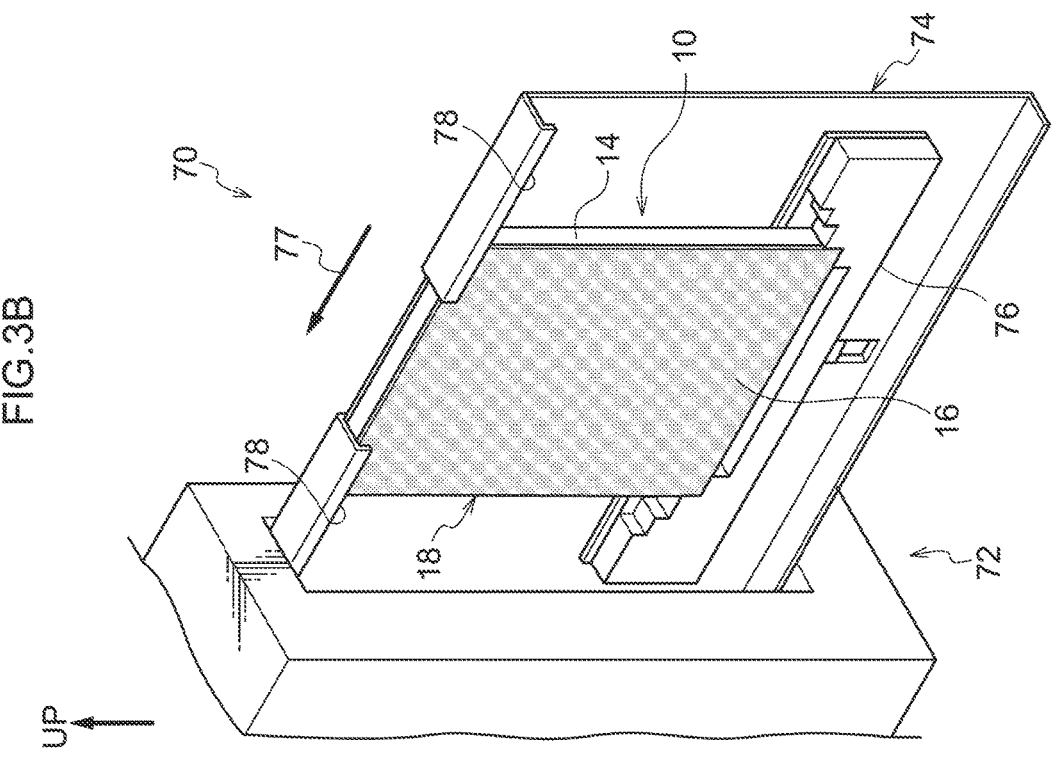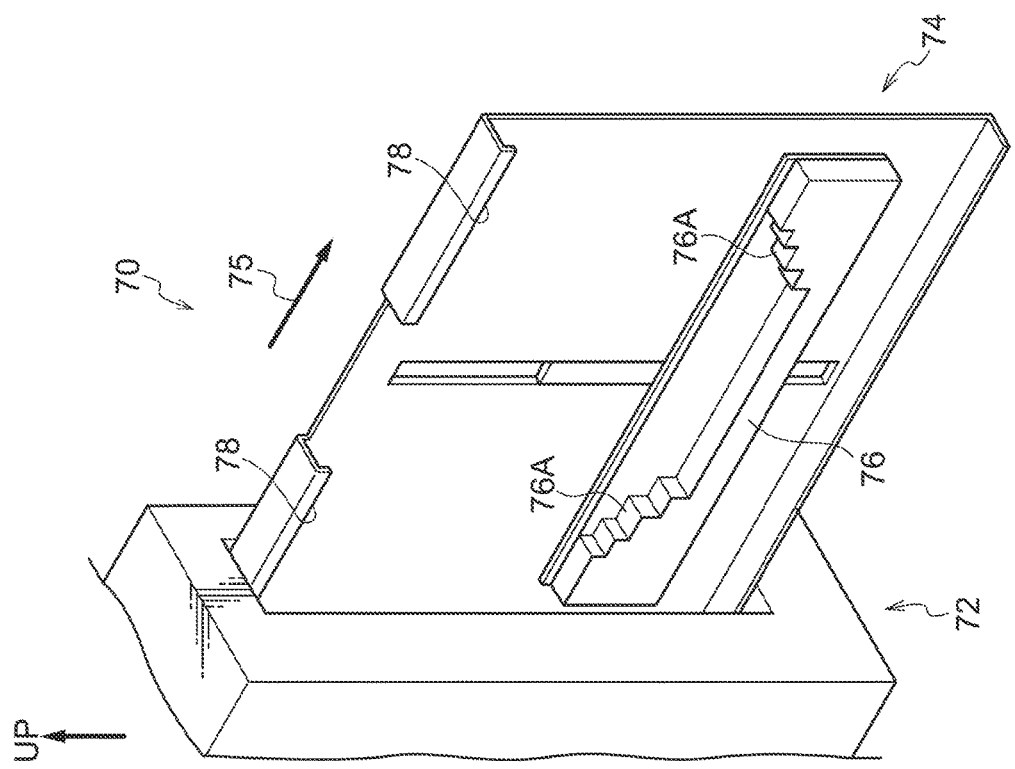

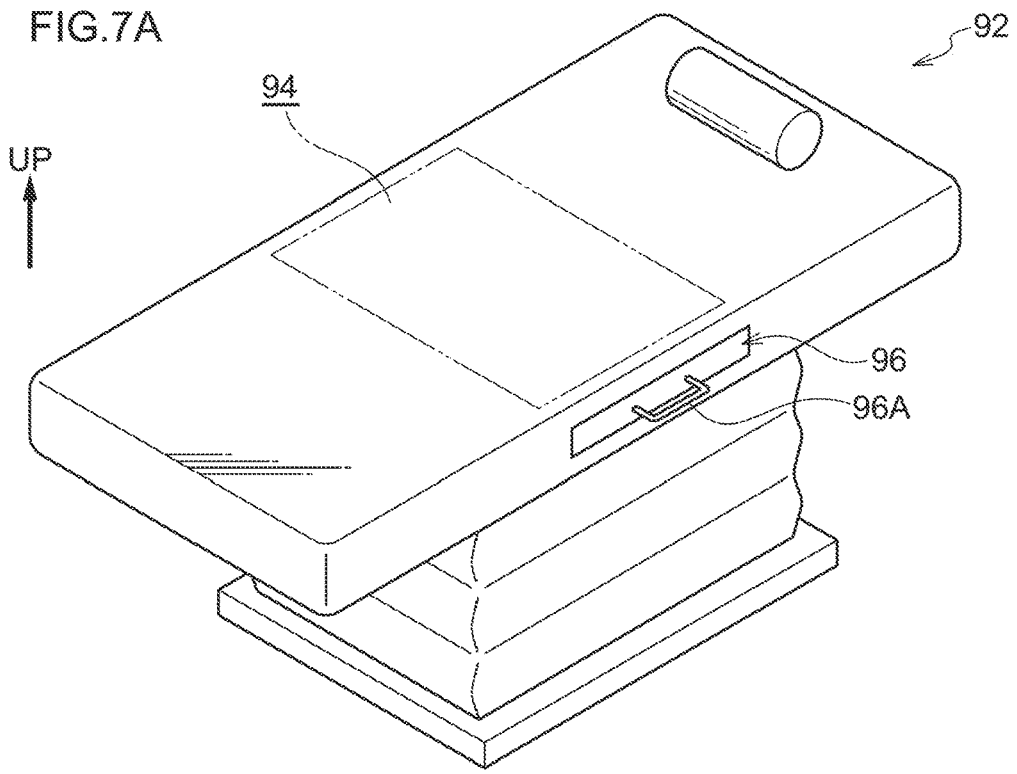
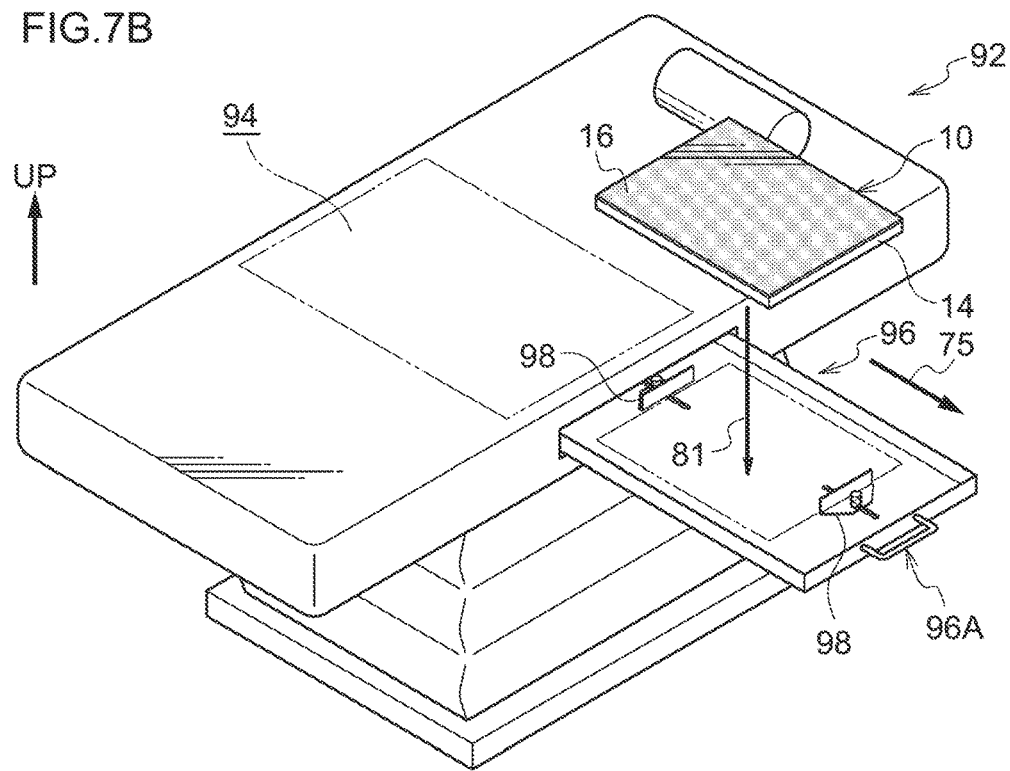

X-RAY IMAGING DEVICE WITH PROTECTIVE COVER

CROSS-REFERENCE TO RELATED APPLICATION

This application is a continuation of and claims priority under 35 USC 120 from U.S. patent application Ser. No. 13/947,094 filed Jul. 21, 2013 and under 35 USC 119 from Japanese Patent Application No. 2012-171283 filed on Aug. 1, 2012, the disclosures of which are incorporated by reference herein.

BACKGROUND

Technical Field

The present invention relates to a radiographic imaging device that forms a radiographic image.

Related Art

Radiographic imaging devices, which are widely used in medical facilities, use radiation to form radiographic images of subjects. A radiographic imaging device may be installed at an imaging stand when being used and form a radiographic image, and when imaging is complete, may be removed and stored in a storage location. For imaging of a subject in a standing position or a reclining position, the radiographic imaging device is mounted, deployed and unmounted at a standing position imaging stand or a reclining position imaging stand. Surfaces of the radiographic imaging device are prone to becoming damaged or soiled during transport and during mounting and unmounting and the like. The radiographic imaging device is an expensive piece of equipment, so it is desirable for it to have a structure that may be used in a state that is free of damage and soiling over long periods.

Accordingly, protective covers have been proposed for preventing damage and soiling of radiographic imaging devices (for example, see Japanese Patent Application Laid-Open (JP-A) No. 2006-293368).

However, the protective cover according to JP-A No. 2006-293368 is formed a size larger than the radiographic imaging device, and encloses the accommodated radiographic imaging device from outer sides thereof. Therefore, external dimensions in a state in which the protective cover is applied are large, and the radiographic imaging device in the protective cover may not be installed at imaging stands that have been used hitherto. As a result, when the radiographic imaging device is to be used, it must be removed from the protective cover to be installed at the imaging stand, which is a burden on medical staff.

SUMMARY

In light of the circumstances described above, an object of the present invention is to provide a radiographic imaging device that may be installed at an imaging stand in a state in which a protective cover that protects a surface of the radiographic imaging device is applied thereto.

A radiographic imaging device according to a first aspect of the present invention includes: a radiographic imaging device main body; and a protective cover that is removably applied to a surface of the radiographic imaging device main body, a thickness including the radiographic imaging device main body in the state in which the protective cover is applied being at most 16 mm.

According to the first aspect of the present invention, the surface of the radiographic imaging device main body is protected by the protective cover that has been removably applied to the surface of the radiographic imaging device main body. In the state in which the protective cover is applied, the thickness including the radiographic imaging device main body is not more than 16 mm.

Therefore, the surface of the radiographic imaging device may be protected with the protective cover, and occurrences of contamination, scratching and the like during transport and during use may be suppressed. Moreover, because the thickness including the radiographic imaging device main body in the state in which the protective cover is applied is not more than 16 mm, interchangeability with conventional cassettes can be assured.

Therefore, the radiographic imaging device may be installed at an imaging stand when being used, without the protective cover being removed.

In a second aspect of the present invention, in a radiographic imaging device according to the first aspect, the radiographic imaging device is a digital radiography cassette.

According to the second aspect of the present invention, the surface of a digital radiography (DR) cassette is protected by the protective cover. A DR cassette has a higher level of electronics than other types of cassette and is higher in cost. Thus, the surfaces of DR cassettes, which have the highest protection requirements, may be protected from scratching, contamination and the like.

In a third aspect of the present invention, in a radiographic imaging device according to the first or second aspect, the protective cover is formed in a sheet shape and is applied at least to a surface of the radiographic imaging device main body at a side at which radiation is to be incident.

Thus, the radiation irradiation side surface of the radiographic imaging device, which is a portion at which scratching, contamination and the like tend to occur, may be protected with the protective cover.

In a fourth aspect of the present invention, in a radiographic imaging device according to any of the first to third aspects, the protective cover is formed with a size that covers the whole area of a surface of the radiographic imaging device main body to which the protective cover is applied.

That is, because the whole area of one surface of the radiographic imaging device is covered with the protective cover, the whole area of the surface at the side covered with the protective cover may be protected from scratching, contamination and the like.

In a fifth aspect of the present invention, in a radiographic imaging device according to any of the first to third aspects, the protective cover is applied to a surface at a side at which radiation is incident when the radiographic imaging device main body is installed at an imaging stand, and to a step portion of at least one side face that is parallel with the radiation.

Thus, when the radiographic imaging device main body is installed at an imaging stand, the surface at the side at which the radiation is incident and step portions in one or more side faces of the radiographic imaging device main body that are parallel to the radiation may be protected from scratching, contamination and the like.

In a sixth aspect of the present invention, in a radiographic imaging device according to any of the first to third aspects, the protective cover is applied to a protective cover recess portion provided in a surface at a side at which radiation is incident when the radiographic imaging device main body is installed at an imaging stand.

That is, the surface at the side at which the protective cover recess portion is formed is covered with the protective cover. Thus, the surface of the radiographic imaging device that is covered with the protective cover, which is to say, the surface of the side at which the radiation is irradiated, may be protected from scratching, contamination and the like. Meanwhile, outer periphery portions of the radiographic imaging device main body may be made thicker.

In a seventh aspect of the present invention, in a radiographic imaging device according to any of the first to sixth aspects, the protective cover is replaceable with another protective cover.

Thus, the protective cover may be exchanged at suitable timings, and an old protective cover may be replaced with a new protective cover. As a result, the radiographic imaging device may be constantly maintained in a clean state without damage.

In an eighth aspect of the present invention, in a radiographic imaging device according to the third aspect, a thermal insulation member is applied to a surface of the radiographic imaging device main body that is at the opposite side thereof from the surface to which the protective cover is applied, and the thickness including the radiographic imaging device main body at a portion at which the protective cover and the thermal insulation member are applied is at most 16 mm.

Thus, the surface of the radiographic imaging device is protected from scratching, contamination and the like by the protective cover, in addition to which thermal conduction from the surroundings of the radiographic imaging device to the interior of the radiographic imaging device during use of the radiographic imaging device is suppressed by the thermal insulation member.

Therefore, rises in the temperatures of electronic components inside the radiographic imaging device may be suppressed, and consistent imaging performance may be assured. Moreover, the radiographic imaging device may be installed at an imaging stand at a time of use without the protective cover being removed.

In a ninth aspect of the present invention, in a radiographic imaging device according to the eighth aspect, a thermal insulation member cover that covers the thermal insulation member is applied to a surface of the thermal insulation member applied to the radiographic imaging device main body, and the thickness including the radiographic imaging device main body in the state in which the protective cover and the thermal insulation member cover are applied is at most 16 mm.

According to the ninth aspect of the present invention, the surface of the radiographic imaging device is protected by the protective cover and the surface of the thermal insulation member is protected by the thermal insulation member cover.

Thus, occurrences of scratching, contamination and the like of the surface of the radiographic imaging device are suppressed. In addition, occurrences of scratching, contamination and the like of the surface of the thermal insulation member are suppressed, and a drop in insulation performance can be suppressed. Moreover, the radiographic imaging device may be installed at an imaging stand at a time of use without the protective cover being removed.

In a tenth aspect of the present invention, in a radiographic imaging device according to any of the first to ninth aspects, the protective cover is formed with any one of a resin sheet, a resin sheet containing reinforcing fibers, a silicone sheet or a fluororesin sheet.

Thus, a material of the protective cover may be suitably selected in accordance with usage objectives and usage environments.

In an eleventh aspect of the present invention, in a radiographic imaging device according to any of the first to ninth aspects, the protective cover is formed with an antibacterial sheet provided with antibacterial capability.

Thus, proliferations of bacteria at the surface of the protective cover may be suppressed.

Because the present invention is configured as described above, a radiographic imaging device in a state in which a protective cover that protects a surface is applied may be installed without alteration at an imaging stand.

BRIEF DESCRIPTION OF THE DRAWINGS

Exemplary embodiments of the present invention will be described in detail based on the following figures, wherein:

FIG. 3A is a partial magnified view of the mounting portion, showing the state in which the mounting portion is pulled out;

FIG. 3B is a partial magnified view of the mounting portion, showing a state in which the radiographic imaging device is installed at the mounting portion;

FIG. 7A is a perspective view of a reclining position stand at which the radiographic imaging device in accordance with the first exemplary embodiment of the present invention is installed, showing a state in which a mounting portion is accommodated;

FIG. 7B is a perspective view of the reclining position stand at which the radiographic imaging device in accordance with the first exemplary embodiment of the present invention is installed, showing a state in which the mounting portion is pulled out;

DETAILED DESCRIPTION

First Exemplary Embodiment

A radiographic imaging device 10 in accordance with a first exemplary embodiment of the present invention is described using FIG. 1A to FIG. 7B.

Figure 1A:
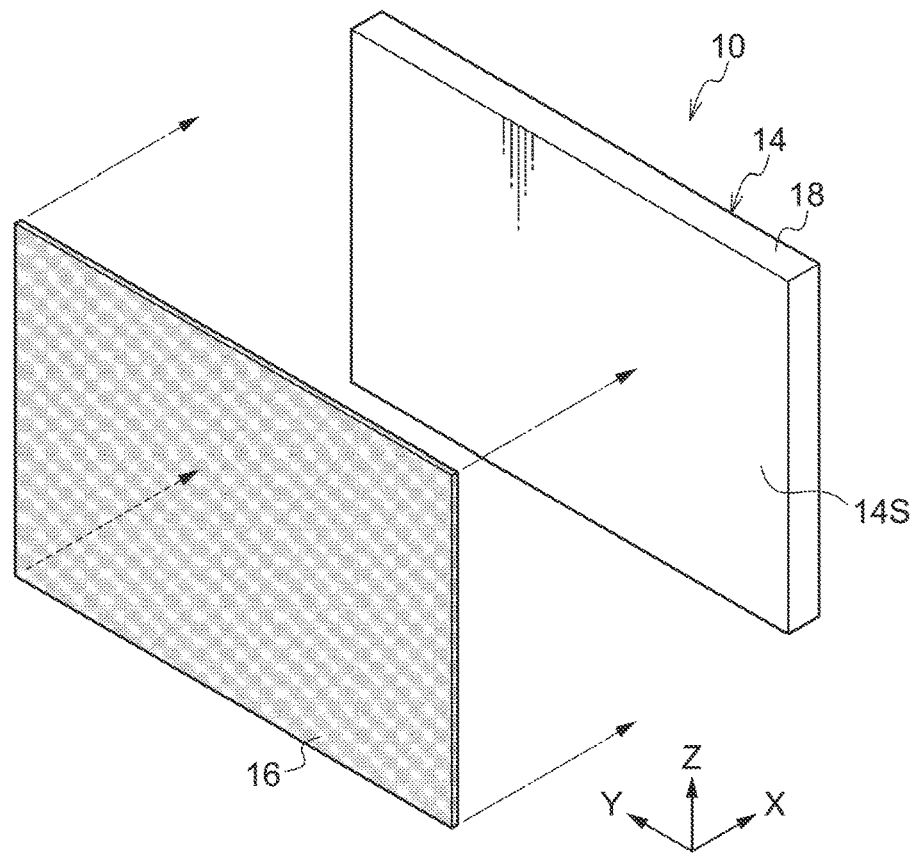
FIG. 1A is an exploded perspective diagram showing the basic structure of a radiographic imaging device in accordance with a first exemplary embodiment of the present invention.
Figure 1B:
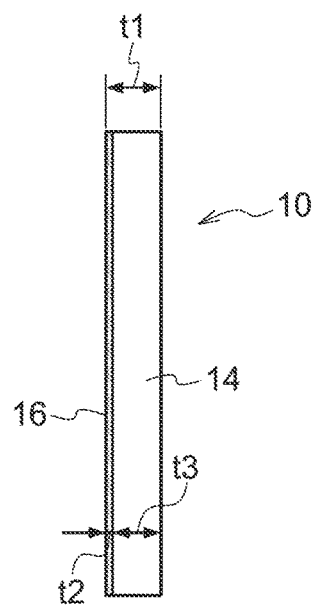
FIG. 1B is a side view of the radiographic imaging device in accordance with the first exemplary embodiment of the present invention.
Figure 4:
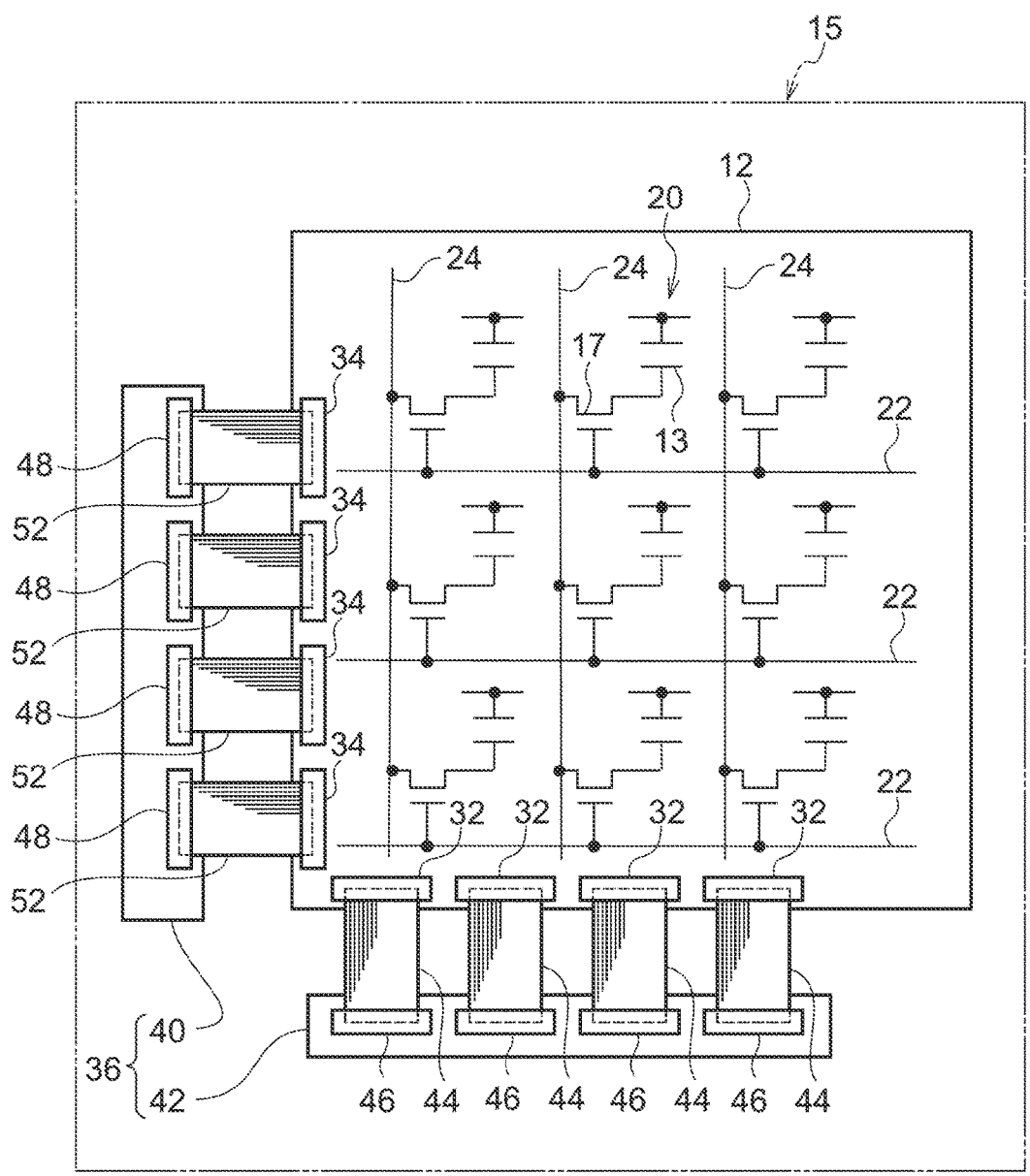
FIG. 4 is a circuit diagram of a radiation detection component that is provided inside a casing of the radiographic imaging device in accordance with the first exemplary embodiment of the present invention.
Figure 5:
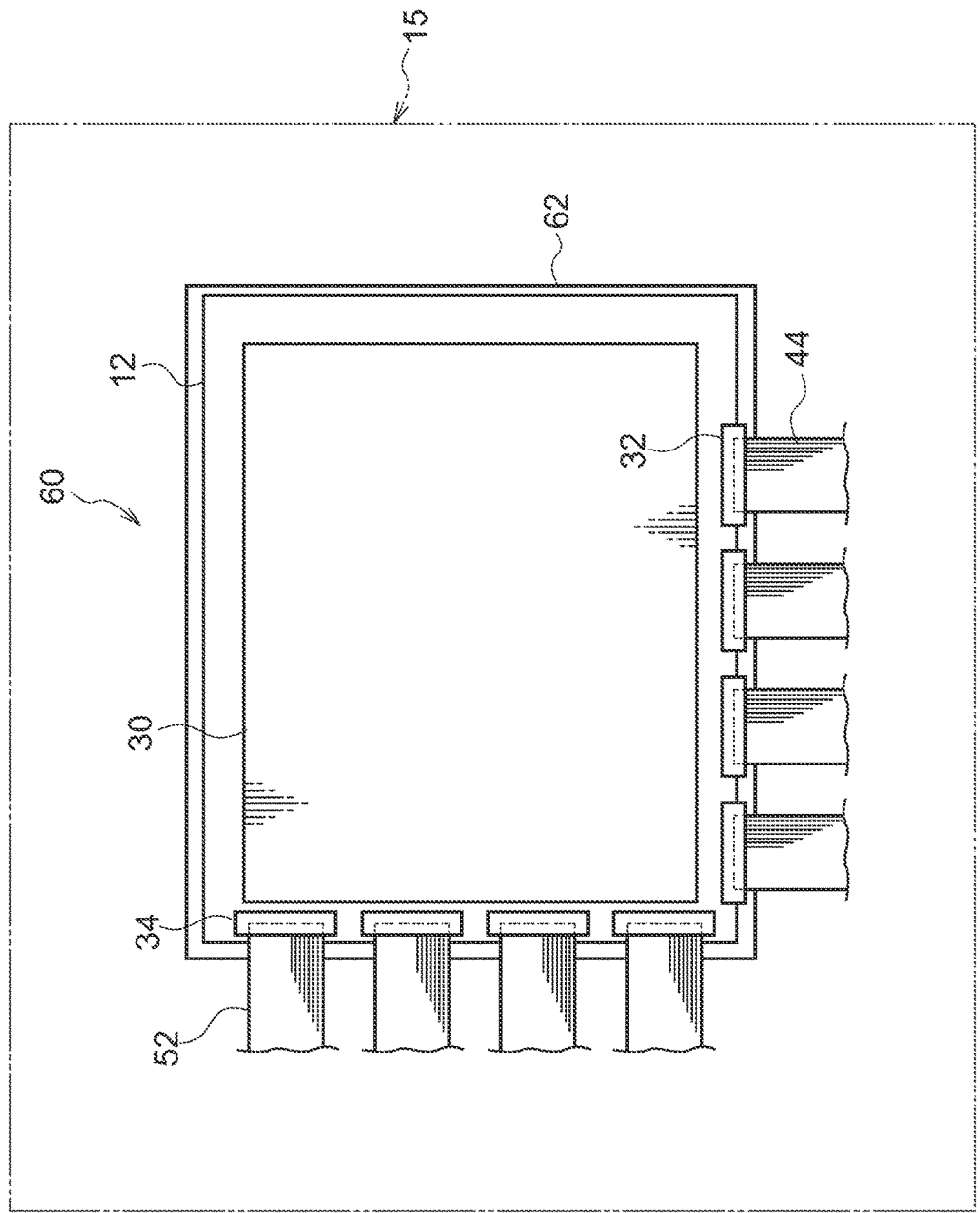
FIG. 5 is a plan diagram showing connection portions of the radiation detection component inside the casing of the radiographic imaging device in accordance with the first exemplary embodiment of the present invention.
Figure 6:
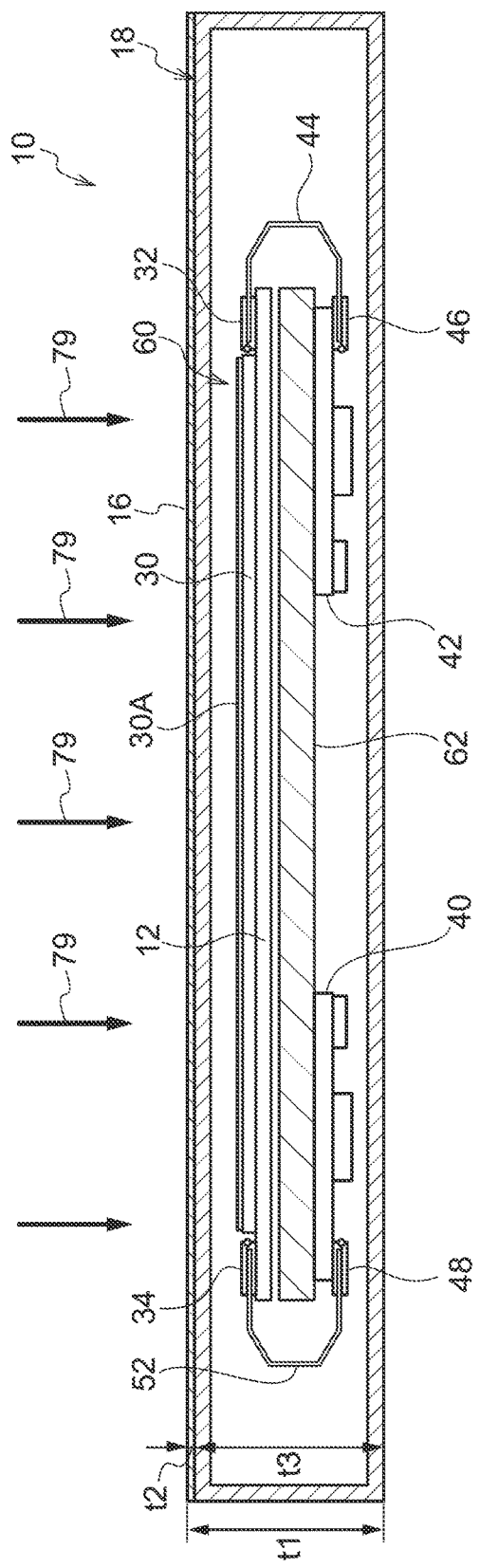
FIG. 6 is a sectional diagram, cut along plane X-Z in FIG. 1, of the radiographic imaging device in accordance with the first exemplary embodiment of the present invention.

FIG. 1A and FIG. 1B are external views of the radiographic imaging device 10 according to the present exemplary embodiment, FIG. 2A, FIG. 2B, FIG. 3A and FIG. 3B are circuit diagrams showing electronic structures of a radiographic imaging device main body 14, FIG. 4 is a sectional diagram showing internal structure of the radiographic imaging device 10, FIG. 5 and FIG. 6 are perspective views of a standing position stand, and FIG. 7A and FIG. 7B are perspective views of a reclining position stand.

As shown in the perspective diagram of FIG. 1A and the side view of FIG. 1B, the radiographic imaging device 10 (hereinafter referred to as "the covered cassette") includes the radiographic imaging device main body 14 (hereinafter referred to as "the cassette"), which detects radiation and forms a radiographic image, and a protective cover 16, which is adhered to one surface 14S of the cassette 14 with an adhesive.

The cassette 14 is portable and includes a casing 18 that is formed in a flat board shape with a thickness of t3. Radiographic imaging components that detect radiation and form a radiographic image, and the like, are accommodated inside the casing 18. The internal structure of the cassette 14 is described below.

The protective cover 16 is formed of a resin sheet with a thickness of t2, and is removably adhered to the single surface 14S of the cassette 14 with an adhesive or the like.

The protective cover 16 is formed with a size that covers the whole area of the surface 14S of the cassette 14 to which the protective cover 16 is to be applied. The protective cover 16 may be easily peeled from the cassette 14, and after peeling is disposed of rather than being re-used.

The radiographic imaging device 10 in which the protective cover 16 is adhered to the cassette 14A is specified such that a thickness t1 including the cassette 14 in the state in which the protective cover 16 is adhered thereto (t1=t2+t3) is smaller than 16 mm, which is a standard value of thickness of the cassette 14 as specified in an ISO standard, a JIS standard (JIS Z4905) and the like.

Therefore, the radiographic imaging device 10 may be installed and used in a mounting portion 74 of a standing position stand (imaging stand) 70 that is currently used, with the surface at the side to which the protective cover 16 is adhered oriented to a side of incidence of radiation. The mounting portion 74 of the standing position stand 70 is shown in FIG. 2A, FIG. 2B, FIG. 3A and FIG. 3B.

Thus, the whole area of the single surface 14S of the cassette 14 is removably covered with the protective cover 16 and protected.

Hence, if the protective cover 16 is subjected to contamination, scratching or the like, the protective cover 16 may be replaced, and the cassette 14 may be protected from occurrences of scratching, contamination and the like. Moreover, by the protective cover 16 being replaced, the radiographic imaging device 10 may be constantly maintained in a clean state without damage, and the cassette 14 may be used over a long period. In addition, mechanical strength of the cassette 14 is reinforced by the protective cover 16.

Because the maximum value of the thickness t1 including the cassette 14 in the state in which the protective cover 16 is adhered thereto is set to not more than the standard value of 15+1 mm, which is to say 16 mm, of the thickness of the cassette 14 as specified in the ISO standard and JIS standard (JIS Z4905), the radiographic imaging device 10 may be installed in an imaging stand without the protective cover 16 being removed.

That is, interchangeability with cassettes that are used without the protective cover 16 being adhered is assured, and the radiographic imaging device 10 may be installed in a conventional imaging stand with the protective cover 16 being kept adhered. As a result, medical staff may be saved the inconvenience of attaching and removing the protective cover 16 to and from the cassette 14.

The thickness of the casing 18 of the cassette 14 is reduced by the thickness t2 of the protective cover 16 (to t3) and the strength of the casing 18 is reduced. However, the fall in mechanical strength may be compensated for with improvement of a reinforcement structure inside the cassette 14, the reinforcing effect of the protective cover 16, and the like.

As a result, medical staff may be saved the inconvenience of attaching and removing the protective cover 16 to and from the cassette 14.

The surface 14S to which the protective cover 16 is adhered is the surface at the side at which radiation is incident when the radiographic imaging device 10 is installed in the mounting portion 74. In general, the surface at the side at which radiation is incident is more likely to be scratched or contaminated or the like. This is because the possibility of direct contact with a patient is higher. Thus, surfaces of the radiographic imaging device 10 may be protected effectively.

The protective cover 16 made of resin may be formed with an antibacterial sheet that is provided with antibacterial capability. Thus, proliferations of bacteria on the surface of the protective cover 16 may be suppressed. Specifically, there are cases of free imaging in which the radiographic imaging device 10 is not installed in an imaging stand for the standing position or the reclining position but is manually held by a technician or the imaging subject or the like, or the cassette 14 is fixed simply using a simple fixing device for imaging, and there are cases of direct contact between the surface 14S and the imaging subject. This is because the subject must be disposed at the radiation incidence side of the radiographic imaging device 10. Thus, it is important for the protective cover 16, which is at the surface 14S at the radiation incidence side, to be bacteria-resistant.

Now, the standing position stand 70 at which the radiographic imaging device 10 is installed is described.

Figure 2B:
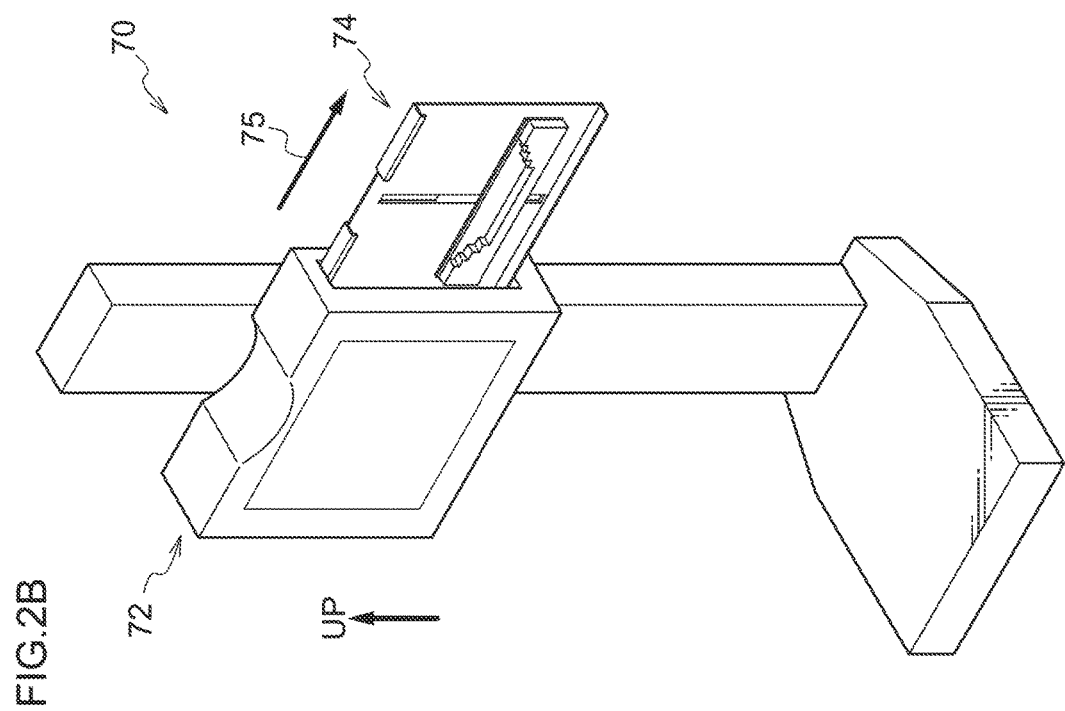
FIG. 2B is a perspective view of the standing position stand at which the radiographic imaging device in accordance with the first exemplary embodiment of the present invention is installed, showing a state in which the mounting portion is pulled out.
Figure 2A:
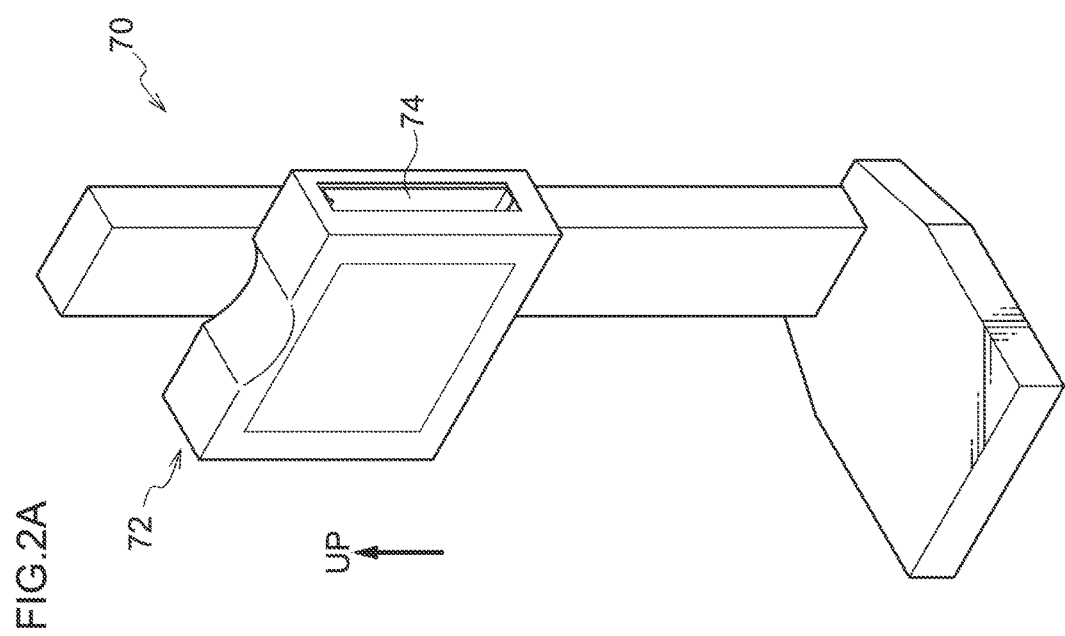
FIG. 2A is a perspective view of a standing position stand at which the radiographic imaging device in accordance with the first exemplary embodiment of the present invention is installed, showing a state in which a mounting portion is accommodated.

As shown in the perspective views in FIG. 2A and FIG. 2B, the mounting portion 74 is provided at an imaging portion 72 of the standing position stand 70, which is used in cases in which an imaging posture is the standing position. The mounting portion 74 can be pulled out from a side face of the imaging portion 72 and the radiographic imaging device 10 can be mounted in the mounting portion 74. Specifically, the mounting portion 74 may be pulled out in the direction of arrow 75.

As shown in the detailed drawings of the mounting portion 74 in FIG. 3A and FIG. 3B, a loading portion 76 is provided at the mounting portion 74. The radiographic imaging device 10 is rested on the loading portion 76, and the loading portion 76 is movable in an up-and-down direction. Steps 76A are formed at the loading portion 76. A lower end portion of the radiographic imaging device 10 fits between the steps 76A. Stepped portions are provided at the steps 76A so as to match up with plural different sizes of the radiographic imaging device 10.

L-shaped hooking portions 78 are provided at an upper end portion of the mounting portion 74. The hooking portions 78 hook on upper end portions of the radiographic imaging device 10 resting on the loading portion 76. With the structure described above, the radiographic imaging device 10 is secured in the up-and-down direction, and the radiographic imaging device 10 is fixed to the standing position stand 70 with the protective cover 16 oriented to the radiation incidence side.

As shown in FIG. 3B, after the radiographic imaging device 10 is mounted at the standing position stand 70, the mounting portion 74 is pushed inside in the direction of arrow 77 (the direction toward the imaging portion 72). When the mounting portion 74 has been pushed in (see FIG. 2A), an X-ray image is captured.

The radiographic imaging device 10 may also be mounted at a reclining position stand 92 (see FIG. 7A and FIG. 7B), which is used when the imaging posture is a reclining position.

As shown in the perspective views in FIG. 7A and FIG. 7B, a mounting portion 96 is provided at an imaging portion 94 of the reclining position stand 92. The mounting portion 96 can be pulled out from a side face of the imaging portion 94 and the radiographic imaging device 10 can be mounted in the mounting portion 96.

The mounting portion 96 is pulled out from the imaging portion 94 in the direction of arrow 75 and the radiographic imaging device 10 is mounted in the mounting portion 96 from the direction of arrow 81. Then, the radiographic imaging device 10 is pushed in into the imaging portion 94, and an X-ray image may be captured.

According to the structure described above, the surface of the cassette 14 is protected by the protective cover 16, and the thickness t1 including the cassette 14 in the state in which the protective cover 16 is adhered thereto is made smaller than the standard value of 16 mm specified in the ISO standard and the JIS standard.

Thus, the radiographic imaging device 10 may be provided that may, in the state in which the protective cover 16 protecting the surface of the cassette 14 is attached, be installed without alteration at the mounting portion 74 that has been used hitherto.

Now, internal structure of the cassette 14 is described. The cassette 14 according to the present exemplary embodiment encompasses any of different systems for recording detected radiation, including computed radiography (CR) cassettes, digital radiography (DR) cassettes and conventional ("film") cassettes. Herein, a DR cassette (hereinafter referred to as an "electronic cassette") 15 is described as a representative example of the cassette 14.

FIG. 4 to FIG. 6 show an example of structures inside the casing 18 of the electronic cassette 15. A radiation detection component 12 is provided in the electronic cassette 15. The radiation detection component 12 is provided with upper electrodes, a semiconductor layer and lower electrodes, and numerous pixels 20 are provided in a two-dimensional arrangement in the radiation detection component 12. Each pixel 20 includes a sensor portion 13 that detects light and accumulates electric charges, and a TFT switch 17 for reading out the charges accumulated in the sensor portion 13.

The radiation detection component 12 is also provided with plural scan lines 22 for turning the TFT switches 17 on and off and plural signal lines 24 for reading out the charges accumulated at the sensor portions 13. The scan lines 22 and signal lines 24 are orthogonal to one another.

At the radiation detection component 12 according to the present exemplary embodiment, a scintillator 30 (see FIG. 5 and FIG. 6) formed of GOS, CIS or the like is adhered to a face of the radiation detection component 12. The scintillator 30 includes a light-blocking member 30A (see FIG. 6) that blocks light produced from the face at the opposite side of the scintillator 30 from the side at which the radiation detection component 12 is adhered, in order to suppress leakages of generated light to the exterior.

At the radiation detection component 12, irradiated radiation such as X-rays or the like is converted to light by the scintillator 30 and illuminated onto the sensor portions 13. The sensor portions 13 detect the light illuminated from the scintillator 30 and accumulate charges.

Then, the TFT switches 17 connected to each scan line 22 are turned on, and electronic signals (image signals) representing a radiographic image according to the charge amounts accumulated at the sensor portions 13 flow into the signal lines 24.

Wiring connectors 32 are plurally provided in a row at a side of the radiation detection component 12 at one end in the signal line direction, and connectors 34 are plurally provided in a row at a side of the radiation detection component 12 at one end in the scan line direction. The signal lines 24 are connected to the connectors 32, and the scan lines 22 are connected to the connectors 34.

In the present exemplary embodiment, a control section 36 is provided for controlling radiation detection by the radiation detection component 12 and controlling signal processing of the electronic signals flowing through the signal lines 24. The control section 36 is provided with a signal detection circuit 42 and a scan signal control circuit 40.

A plural number of connectors 46 are provided at the signal detection circuit 42. One end of a flexible cable 44 is electrically connected to the connectors 46. The other end of the flexible cable 44 is connected to the connectors 32. An amplification circuit that amplifies inputted electronic signals is incorporated at each signal line 24. With this structure, the signal detection circuit 42 amplifies electronic signals inputted through the signal lines 24 with the amplification circuits and detects the electronic signals. Thus, the charge amounts accumulated at the sensor portions 13 are detected to serve as information of the pixels 20 constituting an image.

Connectors 48 are provided at the scan signal control circuit 40. One end of a flexible cable 52 is electrically connected to the connectors 48. The other end of the flexible cable 52 is connected to the connectors 34. Thus, the scan signal control circuit 40 outputs control signals to the scan lines 22 for turning the TFT switches 17 on and off.

As shown in FIG. 5, the electronic cassette 15 according to the present exemplary embodiment includes an imaging section 60 that captures a radiographic image represented by the irradiated radiation. In the imaging section 60, the radiation detection component 12 is disposed at one face of a support substrate 62 (see FIG. 6), which is formed in a flat board shape, and the signal detection circuit 42 and scan signal control circuit 40 corresponding with the radiation detection component 12 are disposed at the other face of the support substrate 62.

Now, principles of operation of the electronic cassette 15 according to the present exemplary embodiment are described. As shown in FIG. 6, when, for example, an X-ray image is to be captured by the electronic cassette 15, X-rays 79 that have passed through a subject are irradiated onto the radiation detection component 12.

At the radiation detection component 12, the irradiated X-rays 79 are converted to light by the scintillator 30, and the light is illuminated onto the sensor portions 13. The sensor portions 13 detect the light illuminated from the scintillator 30 and accumulate charges.

As shown in FIG. 4, at a time of image read-out, "on" signals (+10 to +20 V) are successively applied from the scan signal control circuit 40 to gate electrodes of the TFT switches 17 of the radiation detection component 12 via the scan lines 22.

Thus, the TFT switches 17 of the radiation detection component 12 are successively turned on, and electronic signals corresponding to the charge amounts accumulated at the sensor portions 13 flow out into the signal lines 24. On the basis of the electronic signals flowing into the signal lines 24 of the radiation detection component 12, the signal detection circuit 42 detects the charge amounts accumulated at the sensor portions 13 to serve as information of the pixels 20 constituting the image. Thus, image information representing an image expressed by the radiation irradiated onto the radiation detection component 12 is obtained.

In the present exemplary embodiment, a case is described in which the protective cover 16 is applied to a facing surface at the side of the cassette 14 at which the radiation is incident. However, this is not limiting, and the protective cover 16 may be applied to a surface at the opposite side of the cassette 14 from the side at which the radiation is incident. Further, the protective cover 16 may be applied to the surfaces on both sides of the cassette 14.

The protective cover 16 may have the form of a bag so as to cover the whole of the cassette 14 (in which case t1=2×t2+t3).

In the present exemplary embodiment, an example is described in which the protective cover 16 is a resin sheet. However, this is not limiting, and the protective cover 16 may be formed of any one of a resin sheet containing reinforcing fibers, a silicone sheet, or a fluororesin sheet.

Accordingly, the material of the protective cover 16 may be suitably selected in accordance with usage objectives and usage environments.

While it has been recited that the cassette 14 encompasses any of computed radiography (CR) cassettes, digital radiography (DR) cassettes and conventional ("film") cassettes, providing the protective cover 16 has particularly significant benefits for the above-described DR cassette, because this cassette includes many electronic components and the scintillator and is very high in cost. In the case of a CR cassette or a conventional cassette, a damaged casing surface may be replaced, or the external casing itself may be replaced. In the case of a DR cassette, replacing the cassette because of a damaged surface is too expensive but, because a very large number of electronic components and the like are contained, disassembly just to replace the casing is difficult. Therefore, particularly when the protective cover 16 is included at a DR cassette, the possibility of easy replacement of the protective cover 16 in a hospital is good for user convenience.

Second Exemplary Embodiment

Figure 8A:
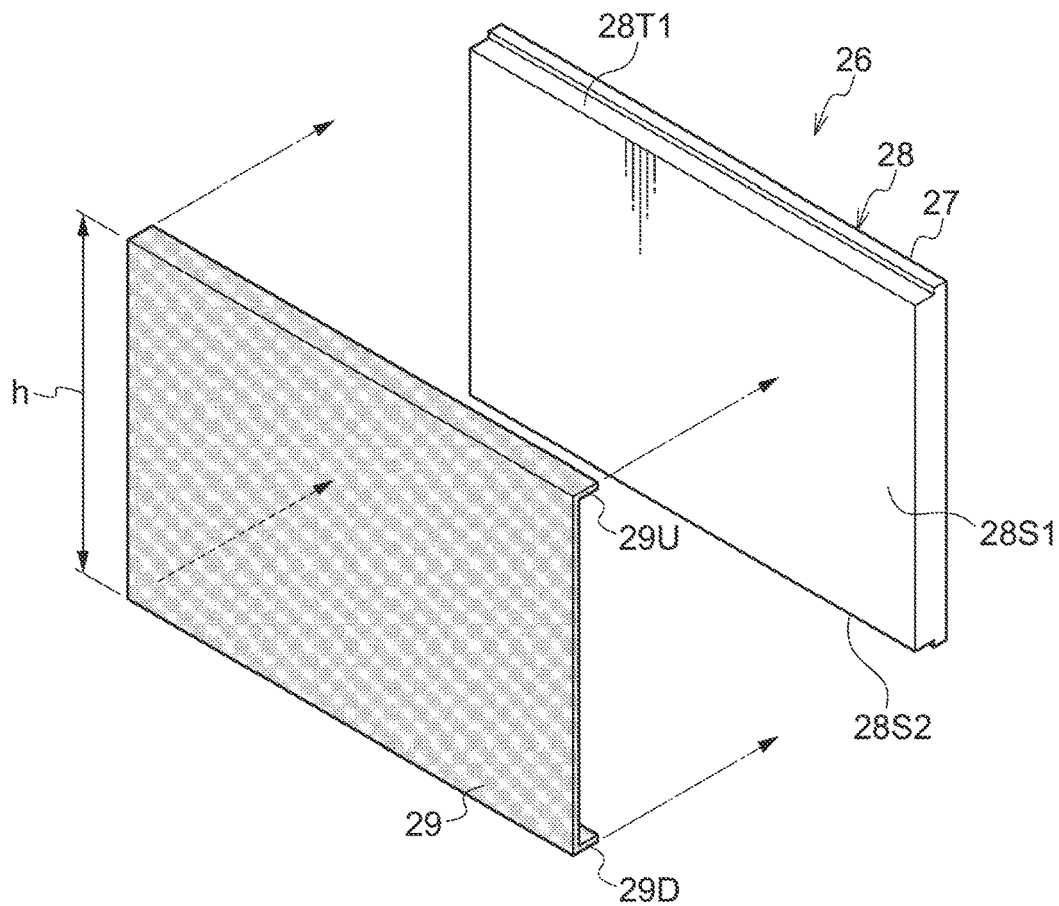
FIG. 8A is an exploded perspective diagram showing the basic structure of a radiographic imaging device in accordance with a second exemplary embodiment of the present invention.
Figure 8B:
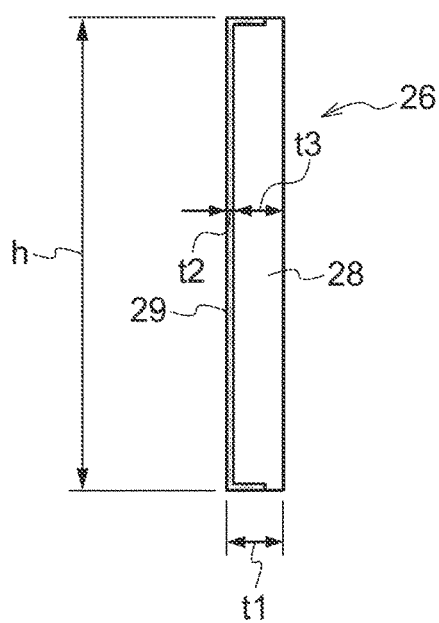
FIG. 8B is a side view of the radiographic imaging device in accordance with the second exemplary embodiment of the present invention.

As shown in the external perspective diagram of FIG. 8A and the side view of FIG. 8B, a radiographic imaging device 26 according to the second exemplary embodiment differs from the cassette 14 according to the first exemplary embodiment in that a protective cover 29 is applied both to surface 28S1 and 28S2 of a cassette 28 and to two opposing side faces 28T1 of the cassette 28. This difference is the focus of description.

The radiographic imaging device (covered cassette) 26 is equipped with the cassette 28 and the protective cover 29. The protective cover 29 is a resin sheet with thickness t2. Opposing end portions 29U and 29D of the protective cover 29 are inflected toward the cassette 28.

The cassette 28 is formed in a flat board shape, including a casing 27 with a thickness of t3. The cassette 28 includes step portions, at which the cassette 28 is formed to be shorter by a dimension equal to a thickness t2 of the protective cover 29, at portions of opposing side faces 28T1 and 28T2 of the casing 27. The thickness of the covered cassette 26, summing the thickness t2 of the protective cover 29 and the thickness t3 of the cassette 28, is t1 (t1=t2+t3).

Accordingly, even if the inflected portions of the protective cover 29 are adhered to the side faces 28T1 and 28T2, protrusion of the protective cover 29 beyond the side faces 28T1 and 28T2 can be suppressed. Thus, the side faces 28T1 and 28T2 may be protected by the protective cover 29 without increasing a height dimension h. If operation portions are formed at the side face 28T1 of the cassette 28 or the side face 28T2, the inflected portion of the protective cover 29 may be cut away by the necessary dimensions.

In the present exemplary embodiment, adhesion of the protective cover 29 to the one surface 28S of the cassette 28 is the same as in the first exemplary embodiment, and is not described here.

Thus, the whole area of the surface 28S of the radiographic imaging device and the surfaces of the opposing side faces 28T1 and 28T2 of the radiographic imaging device main body that are covered with the protective cover 29 may be protected from scratching, contamination and the like.

Other points are the same as in the first exemplary embodiment so are not described here.

Third Exemplary Embodiment

Figure 9A:
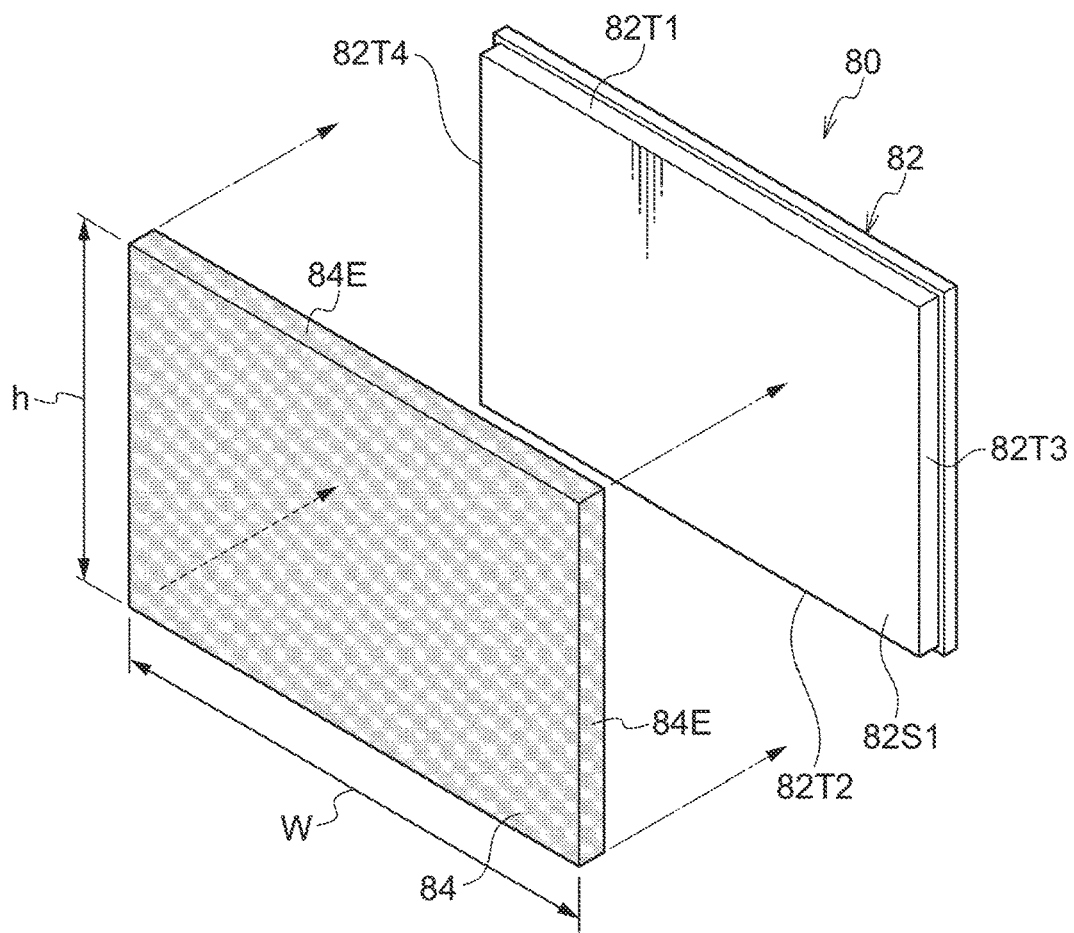
FIG. 9A is an exploded perspective diagram showing the basic structure of a radiographic imaging device in accordance with a third exemplary embodiment of the present invention.
Figure 9B:
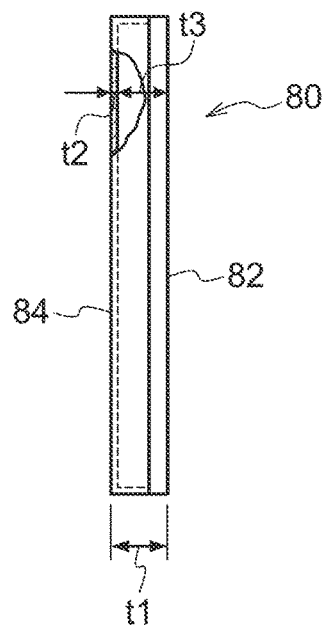
FIG. 9B is a side view of the radiographic imaging device in accordance with the third exemplary embodiment of the present invention.

As shown in the external perspective diagram of FIG. 9A and the side view of FIG. 9B, a radiographic imaging device 80 according to the third exemplary embodiment differs from the covered cassette 26 according to the second exemplary embodiment in that a protective cover 84 is applied to surface 82S1 of a cassette 82 and to all of four side faces 82T1, 82T2, 82T3 and 82T4 of the cassette 82. This difference is the focus of description.

The radiographic imaging device (covered cassette) 80 is equipped with the cassette 82 and the protective cover 84. The protective cover 84 is a resin sheet with thickness t2. Four end portions 84E of the protective cover 84 are inflected toward the cassette 82.

The cassette 82 is formed in a flat board shape, including a casing 82 with a thickness of t3. The cassette 82 is formed with step portions, at which the cassette 82 is formed to be shorter by a thickness t2 of the protective cover 84, at portions of the four opposing side faces 82T1, 82T2, 82T3 and 82T4 of the casing 82. The thickness of the covered cassette, summing the thickness t2 of the protective cover 84 and the thickness t3 of the covered cassette, is t1 (t1=t2+t3).

Accordingly, even if the protective cover 84 is adhered to the side faces 82T1, 82T2, 82T3 and 82T4 too, protrusion of the protective cover 84 beyond the side faces 82T1, 82T2, 82T3 and 82T4 can be suppressed. If operation portions are formed at the side faces of the cassette 82, the inflected portions of the protective cover 84 may be cut away by the necessary dimensions.

In the present exemplary embodiment, adhesion of the protective cover 29 to the one surface 82S of the cassette 82 is the same as in the first exemplary embodiment, and is not described here.

Thus, the whole area of the surface 28S of the radiographic imaging device and the surfaces of the four opposing side faces 82T1, 82T2, 82T3 and 82T4 of the radiographic imaging device main body that are covered with the protective cover 84 may be protected from scratching, contamination and the like.

In addition, the cassette 82 may be protected by the protective cover 84 without increasing a height dimension h or a width dimension w.

Other points are the same as in the second exemplary embodiment so are not described here.

Fourth Exemplary Embodiment

Figure 10A:
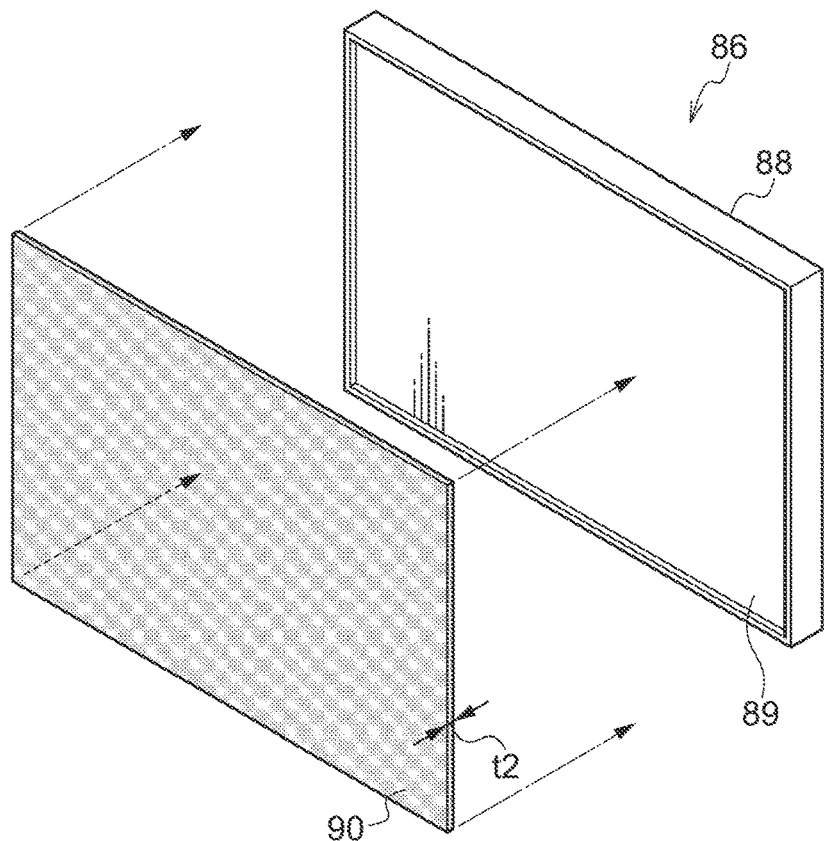
FIG. 10A is an exploded perspective diagram showing the basic structure of a radiographic imaging device in accordance with a fourth exemplary embodiment of the present invention.
Figure 10B:
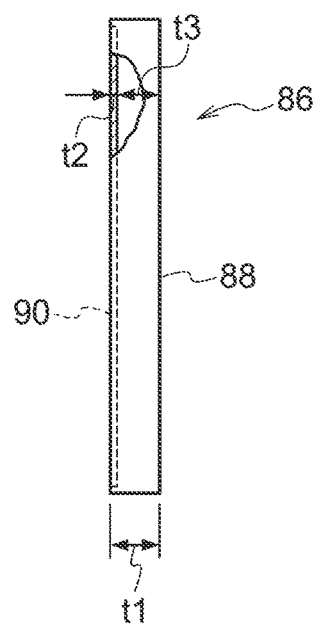
FIG. 10B is a side view of the radiographic imaging device in accordance with the fourth exemplary embodiment of the present invention.

As shown in the external perspective diagram of FIG. 10A and the side view of FIG. 10B, a radiographic imaging device 86 according to the fourth exemplary embodiment differs from the cassette 14 according to the first exemplary embodiment in that a protective cover recess portion 89 is formed in one surface of a cassette 88. This difference is the focus of description. This difference is the focus of description.

At the radiographic imaging device (covered cassette) 86, a protective cover 90 is adhered to the protective cover recess portion 89 provided at the one surface of the cassette 88. The thickness of the cassette 88 at portions at which the protective cover recess portion 89 is formed is t3, and the depth of the protective cover recess portion 89 is equal to or slightly deeper than a thickness t2 of the protective cover 90. Thus, in the state in which the protective cover 90 is adhered in the protective cover recess portion 89, the thickness of the covered cassette 86 is t1 (t1=t2+t3).

Accordingly, at the one surface of the cassette 88 covered with the protective cover 90, the surface at the side of the covered cassette 86 at which the protective cover recess portion 89 is formed in the surface may be protected from scratching, contamination and the like by the protective cover 90. Moreover, the thickness of an outer periphery portion of the cassette 88 may be increased.

Other points are the same as in the first exemplary embodiment so are not described here.

Fifth Exemplary Embodiment

Figure 11:
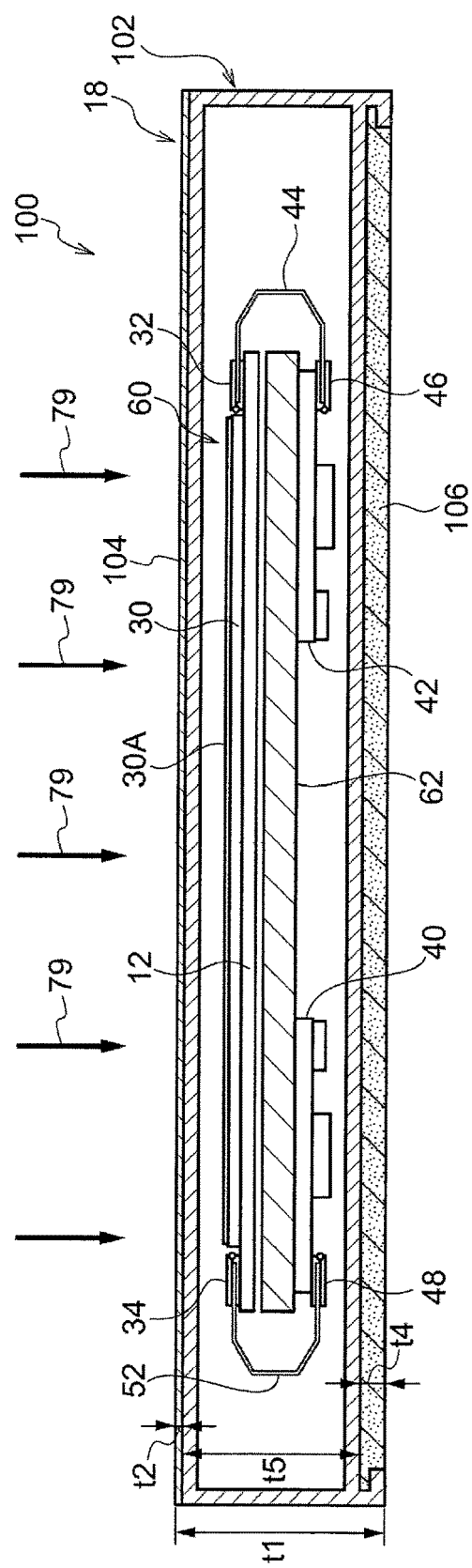
FIG. 11 is a sectional diagram, cut along plane X-Z in FIG. 1, of a radiographic imaging device in accordance with a fifth exemplary embodiment of the present invention.

As shown in the sectional diagram of FIG. 11, a radiographic imaging device 100 according to the fifth exemplary embodiment differs from the radiographic imaging device according to the first exemplary embodiment in that a thermal insulation member 106 is adhered to a surface at the opposite side of a cassette 102 from a surface thereof to which a protective cover 104 is adhered. This difference is the focus of description.

At the radiographic imaging device (covered cassette) 100, the protective cover 104 with thickness t2 is adhered to one surface (the surface at the side at which radiation is incident) of the cassette 102, which has thickness t5, and the thermal insulation member 106 with a thickness of t4 is adhered to the surface at the opposite side of the cassette 102.

A thickness t1 of the covered cassette 100 including the cassette 102 in the state in which the protective cover 104 and thermal insulation member 106 are adhered thereto (t1=t2+t4+t5), is not more than the standard value of $15^{+1}$ mm, which is to say 16 mm, specified in the ISO standard and the JIS standard.

Accordingly, scratching, contamination and the like of the surface of the cassette 102 is suppressed by the protective cover 104. In addition, the conduction of heat from the surroundings of the covered cassette 100 (high-temperature portions of the standing position stand 70 or the reclining position stand 92 or the like) to the interior of the covered cassette 100 when the cassette 102 is being used is suppressed by the thermal insulation member 106.

Therefore, temperature rises of electronic components in the cassette 102 may be suppressed and consistent imaging performance may be assured.

Other points are the same as in the first exemplary embodiment so are not described here.

Sixth Exemplary Embodiment

Figure 12:
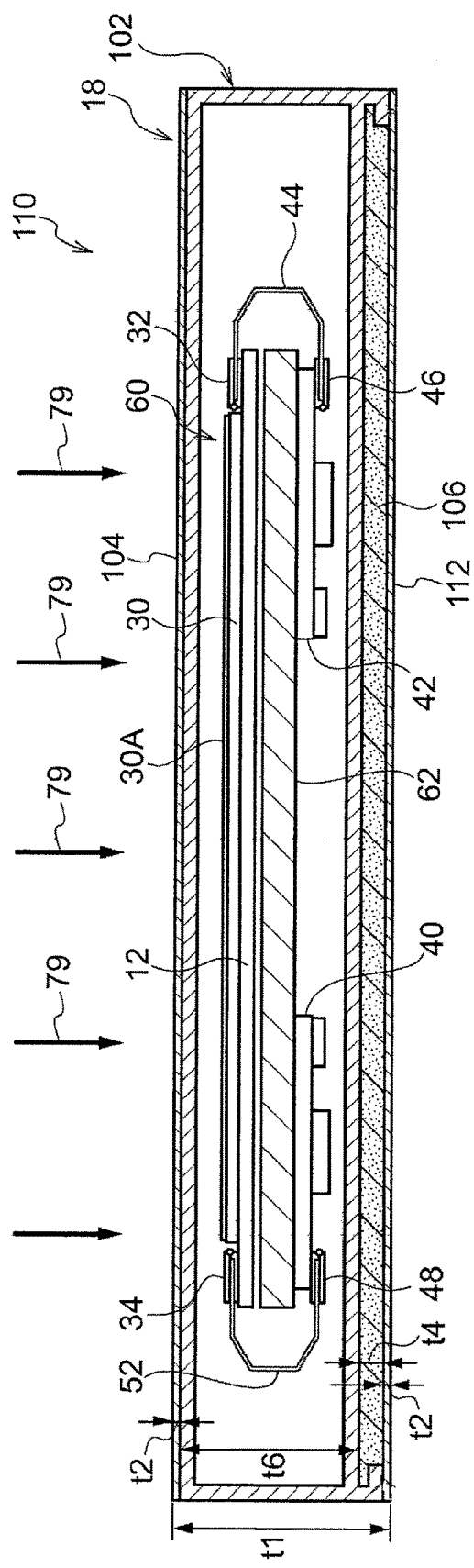
FIG. 12 is a sectional diagram, cut along plane X-Z in FIG. 1, of a radiographic imaging device in accordance with a sixth exemplary embodiment of the present invention.

As shown in the sectional diagram of FIG. 12, a radiographic imaging device 110 according to the sixth exemplary embodiment differs from the radiographic imaging device 100 according to the fifth exemplary embodiment in that the thermal insulation member 106 is adhered to the surface at the opposite side of the cassette 102 from the surface thereof to which the protective cover 104 is adhered, and a thermal insulation member cover 112 is provided at a surface of the thermal insulation member 106. This difference is the focus of description.

At the radiographic imaging device (covered cassette) 110, the protective cover 104 with a thickness of t2 is adhered to the cassette 102, which has a thickness of t6, the thermal insulation member 106 with a thickness of t4 is adhered to the surface of the cassette 102 at the opposite side from the protective cover 104, and the thermal insulation member cover 112 with the thickness t2 is adhered to the surface of the thermal insulation member 106.

That is, a thickness t1 of the radiographic imaging device 110 including the cassette 102 in the state in which the protective cover 104, thermal insulation member 106 and thermal insulation member cover 112 are adhered thereto (t1=t2+t6+t4+t2) is not more than the standard value of $15^+$ mm, which is to say 16 mm, specified in the ISO standard and the JIS standard.

Thus, the surface of the cassette 102 is protected by the protective cover 104 and the surface of the thermal insulation member 106 is protected by the thermal insulation member cover 112. In addition, the conduction of heat from the surroundings of the covered cassette 110 (high-temperature portions of the standing position stand 70 or the reclining position stand 92 or the like) to the interior of the covered cassette 110 when the cassette 102 is being used is suppressed by the thermal insulation member 106.

Accordingly, scratching, contamination and the like of the surface of the cassette 102 is suppressed, and scratching, contamination and the like of the surface of the thermal insulation member is suppressed. Other points are the same as in the fifth exemplary embodiment so are not described here.

What is claimed is:

1. A radiographic imaging device comprising:
    a radiographic imaging device main body; and
    a protective cover that is removably applied to a surface of the radiographic imaging device main body, wherein a thickness of the radiographic imaging device main body, with the protective cover applied, is less than or equal to 16 mm,
    wherein the protective cover is formed as a sheet,
    wherein the protective cover is applied only to a recess portion provided in a surface of the radiographic imaging device at a side of the radiographic imaging device at which x-ray radiation is incident when the radiographic imaging device main body is installed at an imaging stand, and
    wherein in a state in which the protective cover is adhered to the protective cover recess portion, the thickness of the radiographic imaging device is uniform across the radiographic imaging device.

2. The radiographic imaging device according to claim 1, wherein the radiographic imaging device is a digital radiography cassette.

3. The radiographic imaging device according to claim 1, wherein the protective cover is replaceable with another protective cover.

4. The radiographic imaging device according to claim 1, wherein a thermal insulation member is applied to a surface of the radiographic imaging device main body that is at the opposite side thereof from the surface to which the protective cover is applied, and wherein the thickness of the radiographic imaging device, including the radiographic imaging device main body, the protective cover, and the thermal insulation member is less than or equal to 16 mm.

5. The radiographic imaging device according to claim 4, wherein a thermal insulation member cover that covers the thermal insulation member is applied to a surface of the thermal insulation member applied to the radiographic imaging device main body, and wherein the thickness of the radiographic imaging device, including the radiographic imaging device main body, the protective cover, and the thermal insulation member is less than or equal to 16 mm.

6. The radiographic imaging device according to claim 1, wherein the protective cover comprises any one of a resin sheet, a resin sheet containing reinforcing fibers, a silicone sheet or a fluororesin sheet.

7. The radiographic imaging device according to claim 1, wherein the protective cover comprises an antibacterial sheet provided with antibacterial capability.

* * * * *